United States Patent [19]
Wilson

[11] Patent Number: 5,464,381
[45] Date of Patent: Nov. 7, 1995

[54] INFANT SOOTHING SEAT

[76] Inventor: Christi L. Wilson, 310 Constitution Dr. SW., Poplar Grove, Ill. 61065

[21] Appl. No.: 298,616
[22] Filed: Aug. 31, 1994
[51] Int. Cl.[6] .................................................. A61H 1/00
[52] U.S. Cl. .................. 601/49; 297/184.13; 297/250.1; 601/70
[58] Field of Search .......................... 297/184.13, 250.1; 601/46, 47, 49, 70

[56] References Cited

U.S. PATENT DOCUMENTS

| | | | |
|---|---|---|---|
| 4,023,566 | 5/1977 | Martinmaas | 601/47 |
| 4,785,797 | 11/1988 | Cuervo | 601/60 |
| 4,979,777 | 12/1990 | Takada | 297/250.1 |
| 5,063,912 | 11/1991 | Hughes | 601/47 |
| 5,074,820 | 12/1991 | Nakayama | 601/70 |
| 5,097,822 | 3/1992 | Francis | 601/18 |
| 5,147,109 | 9/1992 | Jolly | 297/250.1 |
| 5,322,343 | 6/1994 | Parker | 297/184.13 |

Primary Examiner—Robert A. Hafer
Assistant Examiner—David J. Kenealy

[57] ABSTRACT

A new and improved infant soothing seat comprised of a sound and motion mechanism having a control panel thereon. The control panel consists of a motion control and a sound control. The control panel contains a battery box therein. The battery box houses four batteries therein representing the power source. The sound and motion mechanism has an internal motion control and an internal sound control. The internal motion control consists of a power switch, a speed control, and a variable speed motor. The power switch couples with the power source and the speed control. The speed control couples with the variable speed motor. The variable motor has an eccentric thereattached. The eccentric functions to provide motion for the seat. The internal sound control consists of a power switch, a volume and tone control, and a speaker. The power switch couples with the volume and tone control and the power source. The volume and tone control couples with the speaker.

1 Claim, 3 Drawing Sheets

INFANT SOOTHING SEAT

BACKGROUND OF THE INVENTION

1. Field of the Invention

The present invention relates to an infant soothing seat and more particularly pertains to simulating the vibrations that occur in an automobile to sooth a restless infant with an infant soothing seat.

2. Description of the Prior Art

The use of infant rockers is known in the prior art. More specifically, infant rockers heretofore devised and utilized for the purpose of pacifying babies are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,785,797 to Cuervo discloses a method and apparatus for therapeutic motion and sound treatment of infants.

U.S. Pat. No. 4,620,334 to Robinson discloses an infant rocker.

U.S. Pat. No. 4,947,832 to Blitzer discloses an apparatus and method for treating or relieving colicky infants.

U.S. Pat. No. 3,529,311 to Crawford discloses a crib bouncer for tranquilizing infants.

U.S. Pat. No. 4,590,631 to Varney discloses an infant rocking device.

While these devices fulfill their respective, particular objective and requirements, the aforementioned patents do not describe an infant soothing seat for simulating the vibrations that occur in an automobile to sooth a restless infant.

In this respect, the infant soothing seat according to the present invention substantially departs from the conventional concepts and designs of the prior art, and in doing so provides an apparatus primarily developed for the purpose of simulating the vibrations that occur in an automobile to sooth a restless infant.

Therefore, it can be appreciated that there exists a continuing need for new and improved infant soothing seat which can be used for simulating the vibrations that occur in an automobile to sooth a restless infant. In this regard, the present invention substantially fulfills this need.

SUMMARY OF THE INVENTION

In the view of the foregoing disadvantages inherent in the known types of infant rockers now present in the prior art, the present invention provides an improved infant soothing seat. As such, the general purpose of the present invention, which will be described subsequently in greater detail, is to provide a new and improved infant soothing seat and method which has all the advantages of the prior art and none of the disadvantages.

To attain this, the present invention essentially comprises a seat having an upper surface, a lower surface, a back surface, and two side surfaces. The upper surface has a detachable sun shade removably secured to a top portion thereof. A U-shaped carrying handle is pivotally secured to the two side surfaces. A plurality of small legs are secured to the lower surface. The back surface has an opening therein. The opening has a plurality of mounting slots therein. The device contains a sound and motion mechanism having a front face, a back face, a top face, a bottom face, a right wall, a left wall, an outer surface and an inner surface. The outer surface of the front face has a control panel thereon. The control panel consists of a motion control, a sound control, and a charge socket. The outer surface of the top face has a plurality of projections and detents secured thereto. The projections and detents align with the plurality of mounting slots of the back surface to secure the sound and motion mechanism within the opening of the seat. The outer surface of the right wall has a speaker grate secured therein. The right wall has an oblong aperture therein. The oblong aperture has a cover slidably secured thereover. The oblong aperture contains a battery box therein. The battery box houses four batteries therein representing the power source. The inner surface of the sound and motion mechanism has an internal motion control and an internal sound control. The internal motion control consists of a power switch, a speed control, and a variable speed motor. The power switch has a wire coupled with the power source and the speed control. The speed control has a wire coupled with the variable speed motor. The variable motor has an eccentric thereattached. The eccentric functions to provide motion for the seat. The internal sound control consists of a power switch, a volume and tone control, and a speaker. The power switch has a wire coupled with the volume and tone control and the power source. The volume and sound control has a wire coupled with the speaker. The speaker is in alignment with the speaker grate. The charge socket is electrically connected to the power source. The charge socket allows the power source to be recharged from an electric source.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved infant soothing seat which has all the advantages of the prior art infant rockers and none of the disadvantages.

It is another object of the present invention to provide a new and improved infant soothing seat which may be easily and efficiently manufactured and marketed.

It is a further object of the present invention to provide a new and improved infant soothing seat which is of durable and reliable construction.

An even further object of the present invention is to provide a new and improved infant soothing seat which is susceptible of a low cost of manufacture with regard to both materials and labor, and which accordingly is then susceptible of low prices of sale to the consuming public, thereby making such an infant soothing seat economically available to the buying public.

Still yet another object of the present invention is to provide a new and improved infant soothing seat which provides in the apparatuses and methods of the prior art some of the advantages thereof, while simultaneously overcoming some of the disadvantages normally associated therewith.

Even still another object of the present invention is to provide a new and improved infant soothing seat for simulating the vibrations that occur in an automobile to sooth a restless infant.

Lastly, it is an object of the present invention to provide a new and improved infant soothing seat comprised of a sound and motion mechanism having a control panel thereon. The control panel consists of a motion control, and a sound control. The control panel contains a battery box therein. The battery box houses four batteries therein representing the power source. The sound and motion mechanism has an internal motion control and an internal sound control. The internal motion control consists of a power switch, a speed control, and a variable speed motor. The power switch couples with the power source and the speed control. The speed control couples with the variable speed motor. The variable motor has an eccentric thereattached. The eccentric functions to provide motion for the seat. The internal sound control consists of a power switch, a volume and tone control, and a speaker. The power switch couples with the volume and tone control and the power source. The volume and tone control couples with the speaker.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
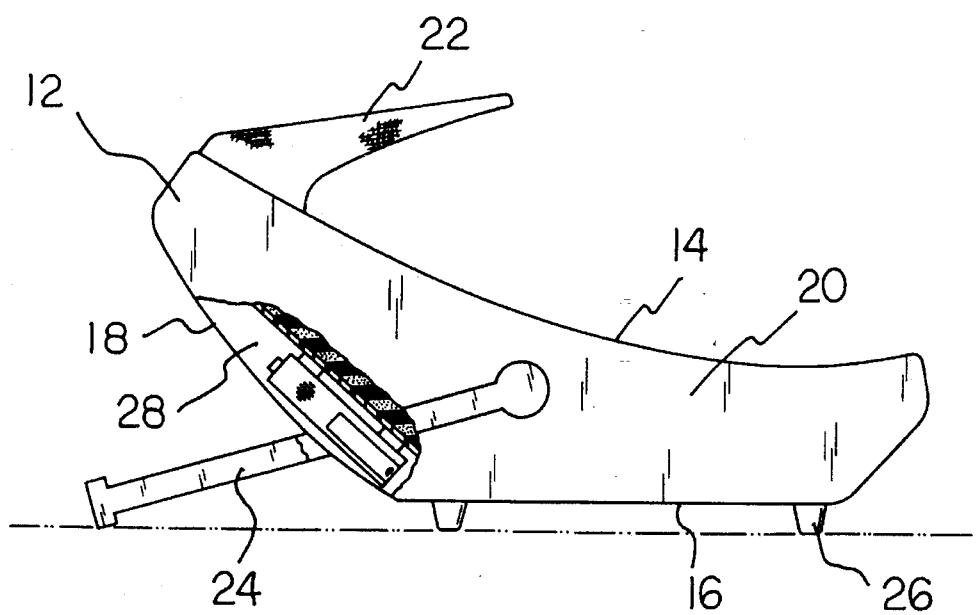
FIG. 1 is a side view of the present invention illustrating the removable sound and motion device.
Figure 2:
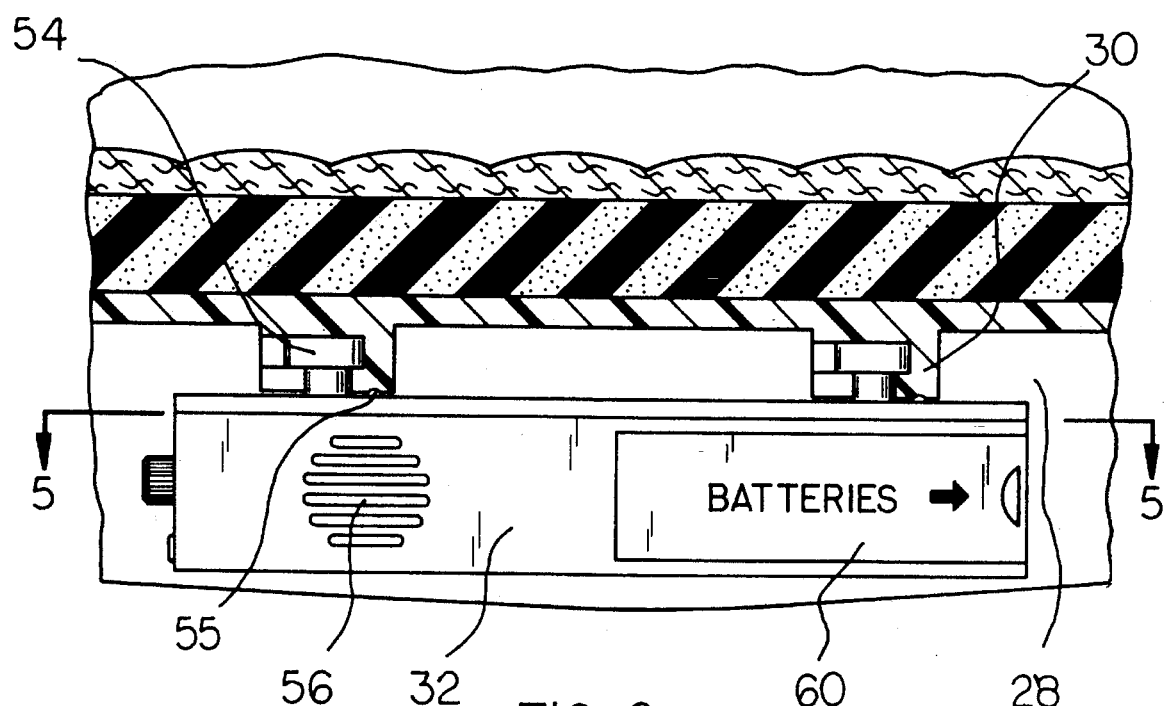
FIG. 2 is a cross-sectional view of the present invention illustrating the securement of the sound and motion device to the baby seat.
Figure 3:
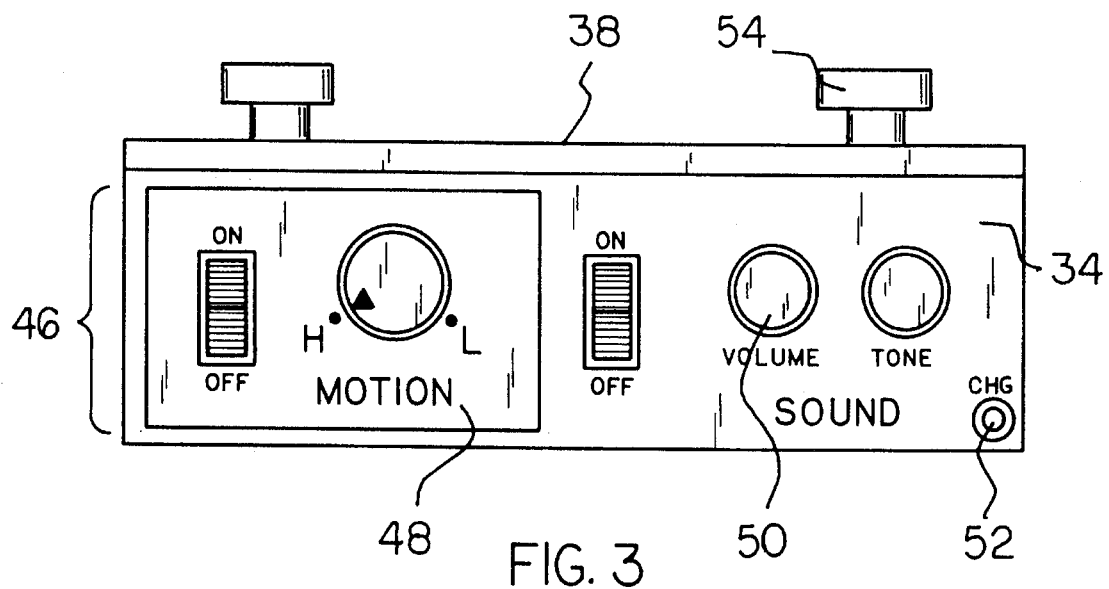
FIG. 3 is a front view of the control panel of the sound and motion device.
Figure 4:
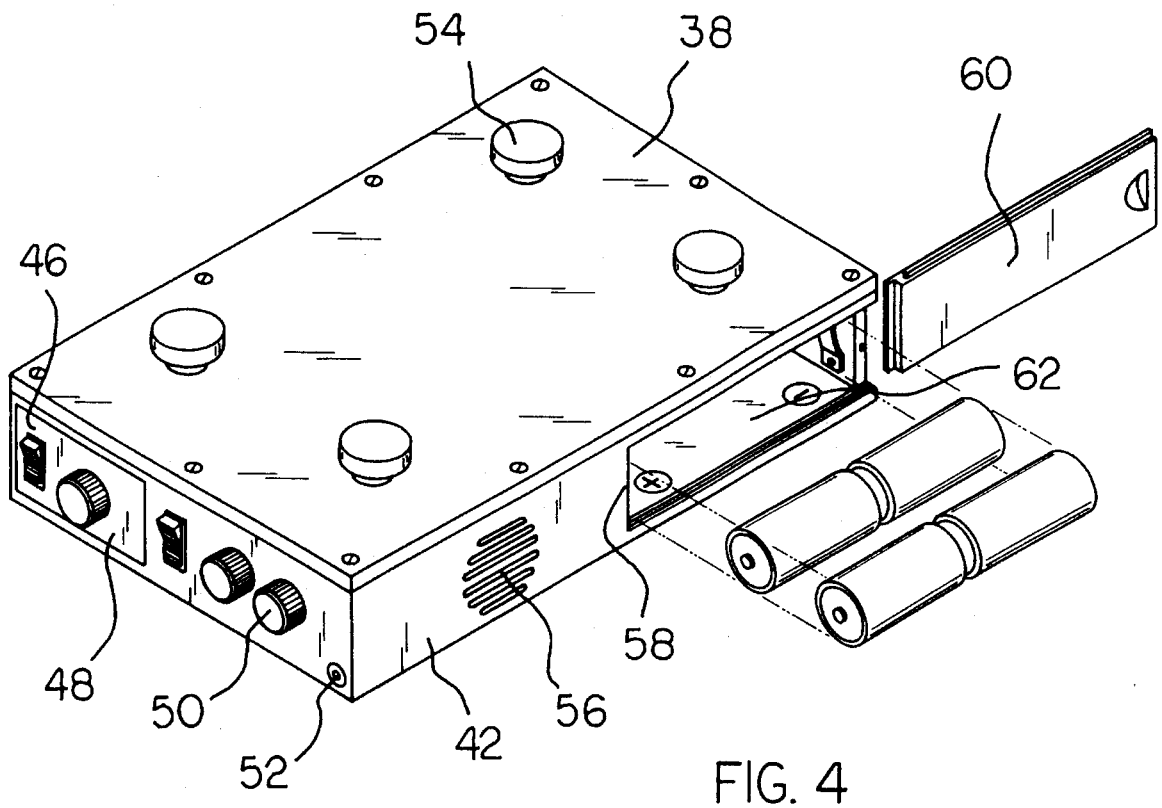
FIG. 4 is a plan view of the present invention showing the battery box.
Figure 5:
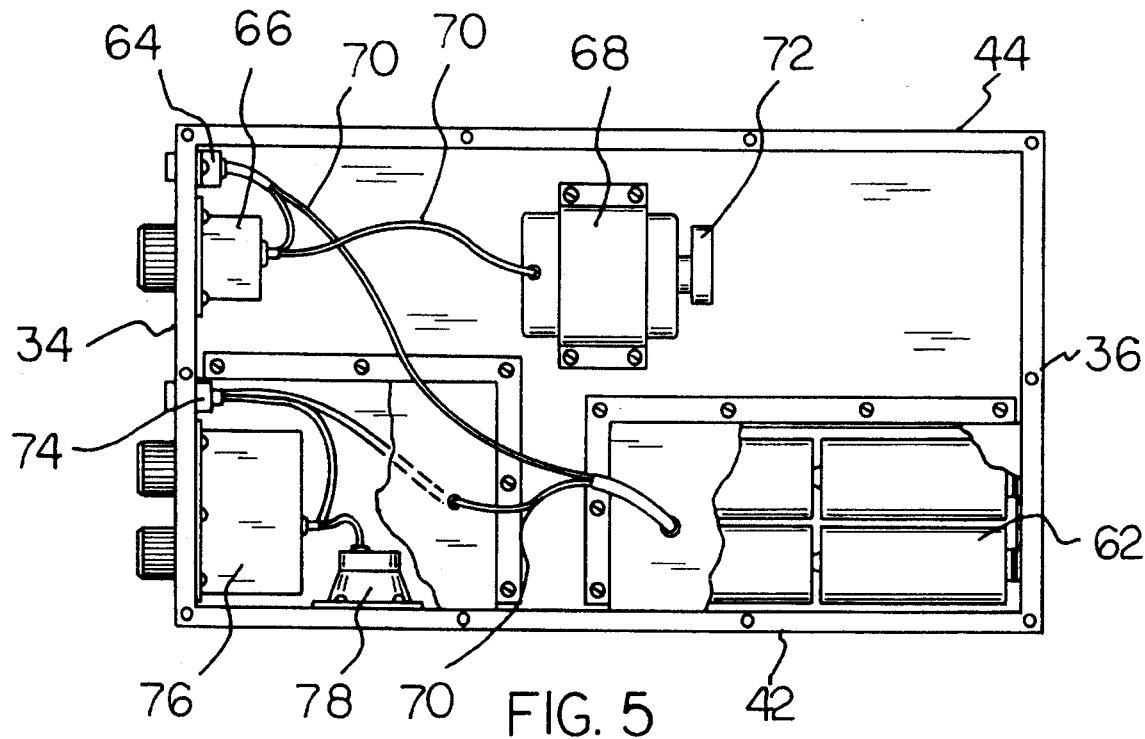
FIG. 5 is a cross-sectional view of the present invention as seen along line 5—5 of FIG. 2.
Figure 6:
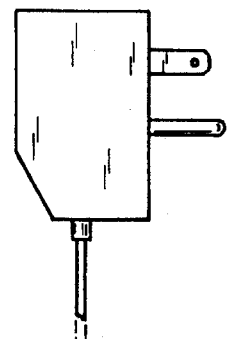
FIG. 6 is a side view of the sound and motion device with the optional charger.

With reference now to the drawings, and in particular, to FIG. 1 thereof, the preferred embodiment of the new and improved infant soothing seat embodying the principles and concepts of the present invention and generally designated by the reference number 10 will be described.

Specifically, it will be noted in the various Figures that the device relates to a new and improved infant soothing seat for simulating the vibrations that occur in an automobile to sooth a restless infant. In its broadest context, the device consists of a seat and a sound and motion mechanism.

The device 10 contains a seat 12 having an upper surface 14, a lower surface 16, a back surface 18, and two side surfaces 20. The upper surface 14 has a detachable sun shade 22 removably secured to a top portion thereof. The sun shade 22 is constructed of a cloth material for use outdoors to protect the infant from harmful sun rays. A U-shaped carrying handle 24 is pivotally secured to the two side surfaces 20. The carrying handle 24 easily allows the seat 12 to become portable and by being pivotable allows the seat 12 to be carried with an infant in the seat. A plurality of small legs 26 are secured to the lower surface 16. The small legs 26 are made of a synthetic rubber material to balance the seat 12 on a flat surface. The back surface 18 has an opening 28 therein. The opening 28 has a plurality of mounting slots 30 therein.

The device 10 contains a sound and motion mechanism 32 having a front face 34, a back face 36, a top face 38, a bottom face 40, a right wall 42, a left wall 44, an outer surface and an inner surface. The outer surface of the front face 34 has a control panel 46 thereon. The control panel 46 consists of a motion control 48, a sound control 50, and a charge socket 52. The outer surface of the top face 38 has a plurality of projections 54 and detents 55 secured thereto. The projections 54 and detents 55 align with the plurality of mounting slots 30 of the back surface 18 to secure the sound and motion mechanism 32 within the opening 28 of the seat 12. The detents 55 prevent the mechanism 32 from becoming disengaged from the seat 12. The outer surface of the right wall 42 has a speaker grate 56 secured therein. The right wall 42 has an oblong aperture 58 therein. The oblong aperture 58 has a cover 60 slidably secured thereover. The oblong aperture contains a battery box 62 therein. The battery box 62 houses four batteries therein representing the power source. The inner surface of the sound and motion mechanism 32 has an internal motion control and an internal sound control. The internal motion control consists of a power switch 64, a speed control 66, and a variable speed motor 68. The power switch 64 has a wire 70 coupled with the power source and the speed control 66. The speed control 66 has a wire 70 coupled with the variable speed motor 68. The variable motor 68 has an eccentric 72 thereattached. The eccentric 72 functions to provide motion for the seat 12. The internal motion control is triggered when the motion control 48 of the control panel 46 is switched to the on position. This triggers the power source which in turn starts the variable speed motor 68. The motor 68 is controlled as to how fast it generates by the speed control 66. The higher the speed control 66 is set, the more rapidly the eccentric 72 will vibrate. The internal sound control consists of a power switch 74, a volume and tone control 76, and a speaker 78. The power switch 74 has a wire 70 coupled with the volume and tone control 76 and the power source. The volume and tone 76 control has a wire 70 coupled with the speaker 78. The speaker 78 is in alignment with the speaker grate 56. The internal sound control is triggered when the sound control 50 of the control panel 46 is switched to the on position. This triggers the power source which in turn activates the volume and tone control 76 which will produce a series of sounds similar to those heard inside a mother's womb. The level of sound and tone is controlled by the volume and tone control 76 which sends the sound signal through the speaker 78. The charge socket 52 is electrically connected to the power source. The charge socket 52 allows the power source to be recharged from an electric source. A simple 110 V charger can amply charge the battery box 62 either in place inside of the seat 12 or when removed.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A new and improved infant soothing seat for simulating the vibrations that occur in an automobile to sooth a restless infant comprising, in combination:

a seat having an upper surface, a lower surface, a back surface, and two side surfaces, the upper surface having a detachable sun shade removably secured to a top portion thereof, a U-shaped carrying handle pivotally secured to the two side surfaces, a plurality of small legs secured to the lower surface, the back surface having an opening therein, the opening having a plurality of mounting slots therein;

a sound and motion mechanism having a front face, a back face, a top face, a bottom face, a right wall, a left wall, an outer surface and an inner surface, the outer surface of the front face having a control panel thereon, the control panel consisting of a motion control, a sound control, and a charge socket, the outer surface of the top face having a plurality of projections and protrusions secured thereto, the projections and protrusions aligning with the plurality of mounting slots of the back surface to secure the sound and motion mechanism within the opening of the seat, the outer surface of the right wall having a speaker grate secured therein, the right wall having an oblong aperture therein, the oblong aperture having a cover slidably secured thereover, the oblong aperture containing a battery box therein, the battery box housing four batteries therein representing the power source, the inner surface of the sound and motion mechanism having an internal motion control and an internal sound control, the internal motion control consisting of a power switch, a speed control, and a variable speed motor, the power switch having a wire coupling with the power source and the speed control, the speed control having a wire coupling with the variable speed motor, the variable speed motor having an eccentric thereattached, the eccentric functioning to provide the motion for the seat, the internal sound control consisting of a power switch, a volume and tone control, and a speaker, the power switch having a wire coupling with the volume and tone control and the power source, the volume and tone control having a wire coupling with the speaker, the speaker in alignment with the speaker grate, the charge socket electrically connected to the power source, the charge socket allowing the power source to be recharged from an electric source.

* * * * *